United States Patent [19]

Miley et al.

[11] Patent Number: 5,973,043

[45] Date of Patent: Oct. 26, 1999

[54] CARBAMOYL SUBSTITUTED ACETALS AND COMPOSITIONS CONTAINING THE SAME

[75] Inventors: John W. Miley, Campobello; C. Charles Carroll; John G. Lever, both of Spartanburg; Nathan A. Mehl, Moore; Joseph M. Salley, Spartanburg, all of S.C.

[73] Assignee: Milliken & Company, Spartanburg, S.C.

[21] Appl. No.: 09/130,921

[22] Filed: Nov. 26, 1997

[51] Int. Cl.$^6$ .................. C08J 3/00; C08K 5/16; C08L 23/00; C07D 323/04
[52] U.S. Cl. ................. 524/199; 524/198; 549/364
[58] Field of Search .................. 524/198, 199; 549/364

[56] References Cited

U.S. PATENT DOCUMENTS

| | | | |
|---|---|---|---|
| 4,314,039 | 2/1982 | Kawai et al. ................. | 525/1 |
| 4,371,645 | 2/1983 | Mahaffey ................. | 524/108 |
| 5,198,484 | 3/1993 | Mannion ................. | 524/108 |
| 5,356,566 | 10/1994 | Kobayashi et al. ................. | 549/364 |

FOREIGN PATENT DOCUMENTS

| | | |
|---|---|---|
| 286522 | 10/1988 | European Pat. Off. . |
| 403292383 | 12/1991 | Japan . |

*Primary Examiner*—Patrick D. Niland
*Attorney, Agent, or Firm*—Terry T. Moyer; Timothy J. Monahan

[57] ABSTRACT

A diacetal of a polyhydric alcohol is provided having at least one carbamoyl substituent bonded to an oxy group of the alcohol. The compound is useful as a nucleating agent in polymer resins and as a gelling agent.

20 Claims, No Drawings

CARBAMOYL SUBSTITUTED ACETALS AND COMPOSITIONS CONTAINING THE SAME

BACKGROUND OF THE INVENTION

This invention relates to carbamoyl derivatives of diacetals of polyhydric alcohols and aromatic aldehydes, which are useful as nucleating agents for polymer resins and as gelling and thickening agents for organic liquids.

The use of nucleating agents to reduce the haze in articles manufactured from crystalline polyolefin resins is well known in the art. Representative acetals of sorbitol and xylitol, which have been employed as clarifying agents, include the following U.S. patents: Hamada, et al., U.S. Pat. No. 4,016,118, dibenzylidene sorbitols; Kawai, et al., U.S. Pat. No. 4,314,039, di(alkylbenzylidene) sorbitols; Mahaffey, Jr., U.S. Pat. No. 4,371,645, di-acetals of sorbitol having at least one chlorine or bromine substituent; Kobayashi, et al., U.S. Pat. No. 4,954,291, distribution of diacetals of sorbitol and xylitol made from a mixture of dimethyl or trimethyl substituted benzaldehyde and unsubstituted benzaldehyde; and Rekers, U.S. Pat. No. 5,049,605, bis(3,4-dialkylbenzylidene) sorbitols including substituents forming a carbocyclic ring.

Methods for manufacturing the acetals may be found in Murai, et al. U.S. Pat. No. 3,721,682 and New Japan Chemical EP 0 497 976.

Although the exact mechanism is not well understood, it is generally believed that the nucleating agent must solubilize and reform into a very fine network within the polyolefin resin. This crystalline network provides nucleation sites, which reduces the size of the spherulites formed in the resin as it cools. Small spherulites do not scatter visible light as effectively as large spherulites, so the nucleated polyolefin resin has improved clarity.

The acetals may be incorporated into a thermoplastic resin as a nucleating agent by blending the acetals and powdered resin together, and then extruding the mixture. One concern that arises during processing is that the acetals can sublimate and redeposit causing "plate out". Consequently, it is often desirable to employ acetals with a relatively low volatility.

As the melting point of the nucleating agent increases, however, it generally becomes necessary to extrude the resin/acetal mixture at higher temperatures. One method of using lower processing temperatures is disclosed in Mannion, U.S. Pat. No. 5,198,484; the acetals are milled to ultrafine particle size, and dissolved in the resin at below their melt temperature. Nevertheless, milling the acetals requires additional processing steps and capital investments in equipment. Further, the solubility of the acetal in the resin may become a factor at operating temperatures below the nucleating agent's melt temperature. Additional considerations in regard to the performance of the acetals as nucleating agents in polymer resins include the cost and availability of the aromatic aldehydes, organoleptics and efficacy.

An alternative clarifying agent for polyolefin resin is disclosed in New Japan Chemical JP 6-256590 (1994). A polyurea containing polymethylene segments of 2 to 12 carbons was found to be an effective crystal clarifying agent at concentrations of 0.01% to 0.05%.

SUMMARY OF THE INVENTION

Therefore, an object of the invention is to provide a nucleating agent/gelling agent which is efficacious in a broad range of thermoplastic resins and organic liquids. Another object of the invention is to provide a carbamoyl derivative of a diacetal of an aromatic aldehyde and a polyhydric alcohol. Another object of the invention is to provide a carbamoyl derivative which is economical to manufacture and use, has low plate out and good organoleptic properties, i.e. low odor and taste transfer characteristics. A further object of the invention is to provide a novel class of compounds which can be readily tailored to achieve desired resin solubility and melt temperature.

Accordingly, a carbamoyl derivative of a diacetal is provided, characterized as a diacetal formed by the condensation reaction of two moles of an aromatic aldehyde and a polyhydric alcohol having five or more hydroxyl groups, having a carbamoyl substituent bonded to an oxy group of the polyhydric alcohol.

The carbamoyl substituted acetal may be used as a nucleating agent by incorporating the compound into a thermoplastic resin under conditions in which the carbamoyl acetal is melted or dissolved in the molten resin, after which the composition is allowed to cool. In another aspect of the invention, the carbamoyl acetal is blended with an organic liquid in an amount sufficient to gel or thicken the liquid.

DETAILED DESCRIPTION OF THE INVENTION

Without limiting the scope of the invention, the preferred embodiments and features are hereinafter set forth. Unless otherwise indicated, all parts and percentages are by weight and conditions are ambient, i.e. one atmosphere of pressure and 25° C. The term "aromatic" refers to single and fused double-ring compounds having at least one unsaturated hydrocarbon ring. The term "aryl" refers to single and fused double ring unsaturated hydrocarbons. Unless otherwise specified, aliphatic hydrocarbons are from 1 to 20 carbon atoms in length, and cycloaliphatic hydrocarbons comprise from 3 to 8 carbon atoms.

All of the United States patents cited in the specification are hereby incorporated by reference.

The carbamoyl acetals of the present invention may be characterized as a diacetal, formed by the condensation reaction of an aromatic aldehyde and a polyhydric alcohol, wherein at least one oxy atom of the alcohol component of the acetal has a carbamoyl substituent bonded thereto. The carbamoyl radical may be "N" substituted with a group selected from aryl, aliphatic and cycloaliphatic groups, which themselves may have from 1 to 4 substituents selected from alkyl, alkoxy, halo and phenyl. Preferably, the carbamoyl radical has one N substituent selected from phenyl, alkyl and cycloalkyl groups. The polyhydric alcohol may have a second free oxy group, as with a hexahydric alcohol or higher, and a second carbamoyl substituent may be bonded to the second oxy group.

The carbamoyl acetals of the present invention may be conveniently made from diacetals of pentahydric and hexahydric alcohols, preferably xylitol and D-sorbitol, respectively, and characterized by the formula:

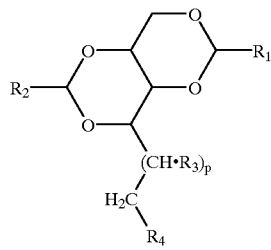

where p is 0 or 1, preferably 1; $R_1$ and $R_2$ are aromatic groups and may be the same or different, preferably $R_1$ and $R_2$ are selected from phenyl and phenyl substituted with from 1 to 3 $C_{1-4}$ alkyl, halo and $C_{3-5}$, alkylene forming a carbocyclic ring with adjacent atoms of an unsaturated hydrocarbon ring; $R_3$ and $R_4$ are selected from the group consisting of —OH and —OC(O)N($R_5$)$R_6$ where $R_5$ is H, aryl, aliphatic or cycloaliphatic, and $R_6$ is H or $R_5$, preferably H; provided that at least one of $R_3$ and $R_4$ is —OC(O)N($R_5$)$R_6$.

The carbamoyl acetal may be synthesized by the addition reaction of an isocyanate and a free hydroxyl group of a diacetal. Monoisocyanates are preferred. Suitable isocyanates may be characterized by the formula R—N=C=O, where R is aryl, aliphatic or cycloaliphatic, preferably phenyl, alkyl, or cycloalkyl, and each R may be further substituted with from 1 to 4 substituent groups selected from phenyl, alkyl, halo and alkoxy. Examples of suitable isocyanates include methylisocyanate, ethylisocyanate, propylisocyanate, isopropylisocyanate, butylisocyanate, tert-butylisocyanate, octylisocyanate, octadecylisocyanate, cyclohexylisocyanate, chloromethylisocyanate, ethoxycarbonylisocyanate, phenylisocyanate, o-tolylisocyanate and allylisocyanate. The diacetal may be reacted with a mixture of isocyanates to provide a carbamoyl acetal with two different carbamoyl substituents.

Diacetals useful in the present invention may be made by the condensation reaction between two moles of an aromatic aldehyde and one mole of a polyhydric alcohol. The aromatic aldehydes are single or fused double ring aldehydes having at least one unsaturated hydrocarbon ring, and include benzaldehyde, naphthaldehyde, indan aldehyde and tetrahydronaphthaldehyde (tetralin aldehyde). The aromatic aldehydes may be unsubstituted or have from one to five substituent groups selected from $C_{1-4}$ alkyl, $C_{1-4}$ alkoxy, hydroxy, halogen, $C_{1-6}$ alkylthio, $C_{1-6}$ alkylsulfoxy, $C_{3-5}$ alkylene forming a carbocyclic ring with adjacent carbon atoms on an unsaturated hydrocarbon ring, carboxyl, ($C_1-C_{20}$ alkyloxy)carbonyl, ($C_1-C_{20}$ alkyloxy)ethyloxycarbonyl, ($C_1-C_{12}$ alkyl)phenyl, halogenated phenyl, ($C_1-C_{12}$ alkoxy)phenyl, ($C_1-C_{12}$ alkyloxy)ethyloxyethyloxycarbonyl and ($C_1-C_{12}$ alkyloxy)ethyloxyethyloxyethyloxycarbonyl groups. Preferably, the aromatic aldehyde is selected from unsubstituted benzaldehyde, benzaldehyde having from one to three substituent groups selected from $C_{1-4}$ alkyl, halogen and $C_{3-5}$ alkylene forming a carbocyclic ring with adjacent carbon atoms on an unsaturated hydrocarbon ring, including p-methyl, p-ethyl, 2,4-dimethyl, 3,4-dimethyl and 2,4,5-trimethyl benzaldehyde, 5-indan aldehyde and 5', 6', 7', 8'-tetrahydro-2-naphthaldehyde. Preferred aromatic aldehydes are represented by the formula:

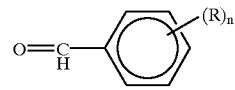

wherein n is 0, 1, 2 or 3, and R is, at each occurrence, selected from $C_{1-4}$ alkyl, halogen, or a three or four membered alkylene group forming a carbocyclic ring with adjacent atoms of the unsaturated parent ring.

Mixtures of the aromatic aldehydes may be provided and will result in a distribution of diacetals having the same or different aromatic components, referred to as symmetric and asymmetric diacetals, respectively. The aromatic aldehydes typically react with the polyhydric alcohol to form acetals in the 1:3 and 2:4 positions.

The polyhydric alcohols have five or more hydroxyl groups. The sugar alcohols represented by the formula $HOCH_2(CHOH)_n CH_2OH$, where n=3–5, have been found to be especially useful. Preferably, the polyhydric alcohol is a pentahydric or hexahydric alcohol, most preferably xylitol or D-sorbitol.

The condensation reaction is typically conducted in a hydrophobic organic liquid medium in the presence of an acid catalyst, as is well known in the art. Diacetals of sorbitol and benzaldehyde and alkyl-substituted benzaldehyde, are commercially available from Milliken Chemical, a division of Milliken & Company, Spartanburg, S.C., U.S.A.

The addition reaction between an isocyanate and alcohol to form a urethane is well known in the art. Preferably, a good solvent for the reactants is employed in the reaction mixture, such as a methyl pyrrolidone, in particular 1-methyl-2-pyrrolidone.

The following example demonstrates the addition reaction between dibenzylidene sorbitol acetal (DBS), having two free hydroxyl groups, and cyclohexyl isocyanate.

EXAMPLE 1

A five liter three-necked round bottom flask, equipped with a stirrer, temperature controller, addition funnel, and nitrogen inlet, was charged with 240 g (0.670 mole) of DBS (Millad® 3905, Milliken Chemical) and 2 L of 1-methyl-2-pyrrolidone (NMP). The contents were stirred and heated to 65° C., and 1.0 g of Bicat V (bismuth 2-ethylhexanoate/neodecanoate mixture, The Shepherd Chemical Company) was added. After the contents were in solution, 209.5 g (1.68 mole) of cyclohexyl isocyanate was added over a 15 minute period under inert atmosphere conditions. The reaction thickened, and additional solvent was added as needed. After two hours, the reaction contents were cooled and filtered. The wet cake was washed with methanol, refluxed in methanol, filtered and dried at 50° C. overnight. The dried product was then processed with a grinding mill equipped with a 0.08 mm ring sieve.

EXAMPLES 2–16

Carbamoyl acetals were synthesized using a variety of diacetals and isocyanates, according to procedures analogous to Example 1 above. The results of Examples 1–16 are summarized in Table I. For a given example, the structure indicated in Table I is believed to be the predominant product, but there may be a distribution of mono- and di-substituted compounds. The melting points shown in Table I were measured using a DSC at a heating rate of 20° C./minute and represent the peak melting point. Note that Example 8 is a comparative product which does not contain the carbamoyl substituent.

TABLE I

[Structure: bicyclic dioxane ring system with R₁ and R₂ substituents at acetal positions, and a -(CH-R₃)ₚ-CH₂-R₄ side chain]

| Example | p | R₁, R₂ | R₃, R₄ | mp (° C.)‡‡ |
|---|---|---|---|---|
| 1 | 1 | phenyl | [—OH, —OC(O)NH-cyclohexyl] | 282 |
| 2 | 1 | [phenyl, 2,4-dimethylphenyl]* | [—OH, —OCONH-i-Pr] | 268 |
| 3 | 1 | 4-(i-Bu)phenyl | —OCONH-n-Pr | 257 |
| 4 | 1 | 3,4-dimethylphenyl | —OCONH-i-Pr | 278 |
| 5 | 0 | 3,4-dimethylphenyl | —OCONH-i-Pr‡ | 246 |
| 6 | 1 | 3,4-dimethylphenyl | —OCONH-t-Bu | 241 |
| 7 | 1 | 3-methoxyphenyl | —OCONH-octadecyl | 163 |
| 8 | 1 | 3,4-dimethylphenyl | —OH | 278 |

TABLE I-continued $$\text{structure with } R_1, R_2, R_3, R_4 \text{ substituents on dioxane rings with } (CH-R_3)_p \text{ and } H_2C-R_4 \text{ side chain}$$

| Example | p | R₁, R₂ | R₃, R₄ | mp (°C.)‡‡ |
|---------|---|--------|--------|------------|
| 9 | 1 | 3,4-dimethylphenyl | [—OH, —OC(O)NH—cyclohexyl] | 289 |
| 10 | 1 | phenyl | [—OH, —OCONH-n-Bu] | 225 |
| 11 | 1 | phenyl | —OCONH-n-Bu | 264 |
| 12 | 1 | 4-fluorophenyl | [—OH, —OC(O)NH—cyclohexyl] | 272 |
| 13 | 1 | phenyl | —OCONH-i-Pr | 287 |
| 14 | 1 | 4-chlorophenyl | —OCONH-n-Pr | 280 |
| 15 | 1 | tetrahydronaphthyl | [—OH, —OC(O)NH—cyclohexyl] | 285 |
| 16 | 1 | 4-ethylphenyl | —OCONH-n-Pr | 280 |

*R₁ and R₂ are a mixture. Diacetal starting material is Gel All DH, New Japan Chemical.
‡R₄ only.
‡‡DSC peak melting point.

The carbamoyl acetal compounds of the present invention may be incorporated into a wide variety of thermoplastic polymer resin compositions, where the compound finds utility as a nucleating and gelling agent. The carbamoyl acetals are particularly useful as nucleating agents in polyolefin resins, which include aliphatic polyolefins and copolymers made from at least one aliphatic olefin and one or more ethylenically unsaturated comonomers. Generally, the comonomers, if present, will be provided in a minor amount, e.g., about 10% or less or even about 5% or less, based upon the weight of the polyolefin. Such comonomers may serve to assist in clarity improvement of the polyolefin, or they may function to include other properties of the polymer. Examples include acrylic acid, methacrylic acid, and esters of the same and vinyl acetate.

Examples of olefin polymers which can be nucleated and whose transparency may be approved according to the present invention include polymers and copolymers of aliphatic mono-olefins containing from 2 to about 6 carbon atoms, which have an average molecular weight of from about 10,000 to about 2,000,000, preferably from about 30,000 to about 300,000, such as polyethylene, including linear low density polyethylene, low density polyethylene and high density polyethylene, polypropylene, crystalline ethylene/propylene copolymer (random or block), poly(1-butene) and polymethylpentene.

Examples of other thermoplastic polymer resins which may be nucleated with the carbamoyl acetal compounds include polyester, including poly(ethylene terephthalate) (PET) and poly(butylene terephthalate) and polyamide, including nylon 6 and nylon 6,6, poly(phenylene sulfide), syndiotactic polystyrene and polyketones having carbonyl groups in their backbone.

Other additives may also be used in the composition of the present invention, provided they do not interfere with the primary benefits. It may even be advantageous to premix these additives with the clarifying agent. Such additives are well known to those skilled in the art and include plasticizers, lubricants, catalysts neutralizers, antioxidants, light stabilizers, colorants, other nucleating agents including sorbitol acetals not having a carbamoyl substituent group, and the like. Some of these additives may provide further beneficial property enhancements, including improved aesthetics, easier processing, and improved stability.

The nucleating agent may be added to the resin at a concentration of from 0.005 to 3 wt. %, preferably 0.01 to 1 wt. %, most preferably 0.025 to 0.5 wt. % of the composition. While higher concentrations of the nucleating agent may be employed, little or no additional advantage is observed.

Concentrates of up to 50 wt. % of the nucleating agent in resin may also be prepared for blending with additional resin prior to molding. Typically, concentrates containing 33 wt. % or less of the nucleating agent in resin are used commercially. The carbamoyl acetals may be compounded with a resin using conventional processes and equipment. The term "compounding" is used broadly to describe the process of dispersing the nucleating agent throughout a resin while the resin is in a molten state, i.e. heated to above its melting temperature. Commercially, compounding is performed in an extruder, such as a single screw extruder, twin screw extruder or Farrel continuous mixer. Extrusion conditions vary depending upon the particular resin.

The resin is usually extruded a second time immediately before being processed into a finished article by, for example, injection molding, extrusion blow molding, injection blow molding, stretch blow molding, compression molding, rotational molding, profile extrusion, sheet extrusion, thermal forming, film extrusion, and film extrusion with orientation.

The following example illustrates the nucleating effect of the carbamoyl acetal of the present invention as measured by $T_c$, the temperature of crystallization, and haze. The $T_c$ was measured using a DSC. Polymer samples were melted and held at 220° C. for 2 minutes and then cooled at 20° C./minute. $T_c$ was the temperature at peak maximum during the crystallization exotherm. The haze of 50 mil (0.05 inches thick) injection molded plaques was measured using a Hunter Hazemeter™.

EXAMPLE 17

Compositions containing various levels of the carbamoyl acetal of Examples 1–16, coadditives (0.05 wt. % Irgafos 168, 0.1 wt. % Irganox 1010, and 0.08 wt. % calcium stearate) and the balance polypropylene homopolymer or polypropylene random copolymer (3% ethylene content) were dry blended in a mechanical mixer, extruded through a single screw extruder at 240° C. and pelletized. Plaques were prepared (0.050 inches thick) by injection molding the pellets at 220° C. The $T_c$ and haze were measured, and the results are reported in Table II.

TABLE II

| (PP) | | | | |
|---|---|---|---|---|
| Polymer | Compound | Concentration (ppm) | Tc (° C.) | Haze* (%) |
| RCP PP | (Control) | — | 90.2 | 61 |
| RCP PP | 1 | 500 | 108.7 | 23 |
| RCP PP | 1 | 750 | 109.1 | 19 |
| RCP PP | 1 | 1000 | 109 | 20 |
| RCP PP | 2 | 1000 | 108.1 | 21 |
| RCP PP | 3 | 3500 | 106.7 | 19 |
| RCP PP | 5 | 1000 | 104.7 | 63 |
| RCP PP | 6 | 2500 | 99.4 | 37 |
| RCP PP | 7 | 1000 | 93.9 | 58 |
| RCP PP | 8 (comparative) | 500 | 99.1 | 45 |
| RCP PP | 8 and 9 | 1000 each | 110.8 | 15 |
| RCP PP | 10 | 1000 | 92.1 | 56 |
| RCP PP | 11 | 1000 | 102.1 | 37 |
| RCP PP | 13 | 1000 | 107.6 | 26 |
| RCP PP | 15 | 1000 | 107.3 | 25 |
| RCP PP | 16 | 1000 | 103.9 | 30 |
| PP | (Control) | — | 102.6 | 64 |
| PP | 1 | 1000 | 119.8 | 30 |
| PP | 2 | 1000 | 118.9 | 30 |
| PP | 15 | 1000 | 119.2 | 35 |

*Average of 10 specimens

EXAMPLE 18

The carbamoyl acetals were tested in linear low density polyethylene (LLDPE) according to the procedure outlined in Example 17, except that 0.05 wt. % sodium stearate was substituted for the coadditives listed and the mixture was extruded and molded at 200° C. The $T_c$ and haze were measured, and the results are reported below in Table III.

TABLE III

| (PE) | | | | |
|---|---|---|---|---|
| Polymer | Compound | Concentration (ppm) | Tc (° C.) | Haze* (%) |
| LLDPE | (Control) | — | 96.2 | 98.9 |
| LLDPE | 3 | 2,500 | 103.1 | 71.6 |
| LLDPE | 10 | 3,000 | 103.8 | 62.1 |
| LLDPE | 11 | 500 | 100.7 | 76.7 |
| LLDPE | 12 | 2,500 | 105.3 | 83.8 |
| LLDPE | 13 | 2,500 | 104.5 | 91.8 |

*Average of 10 specimens

EXAMPLE 19

The carbamoyl acetals were tested in PET according to the method outlined in Example 17 above, except that the coadditives were not added and after dry blending, the mixture was dried in a vacuum oven at 150° C. for three hours prior to extruding, and the mixture was extruded at 270° C. and pelletized. The pellets were not injection molded. The $T_c$ was measured, the Δ intrinsic viscosity (I.V.) was tested for selected samples, and the results are reported below in Table IV. The Δ I.V. reflects changes in the molecular weight of the polymer, such as may be caused by degradation. Intrinsic viscosity measurements were taken with an Ubbelohde viscometer by dissolving approximately 0.1 g of the composition in 25 g of a 60/40 solution of phenol/tetrachloroethane.

TABLE IV (PET)

| Compound | Concentration (ppm) | Tc (° C.) | Δ I.V. |
|---|---|---|---|
| (Control) | — | 152.9 | — |
| 4 | 5,000 | 176.5 | −0.03 |
| 8 (comparative) | 5,000 | 158.5 | −0.06 |
| 12 | 2,500 | 178.4 | not tested |
| 14 | 3,000 | 177.9 | not tested |
| 15 | 5,000 | 178.6 | −0.02 |
| 16 | 5,000 | 177.5 | −0.03 |

EXAMPLE 20

The carbamoyl acetals were tested in nylon 6,6 using the method outlined in Example 17 above, except that the coadditives were not added and, after dry blending, the mixture was dried in a vacuum oven at 80° C. for three hours, and the dry mixture was extruded at 290° C. and pelletized. The pellets were not injection molded. The $T_c$ was measured, and the results are reported below in Table V.

TABLE V (Nylon)

| Compound | Concentration (ppm) | Tc (° C.) |
|---|---|---|
| (Control) | — | 223 |
| 1 | 2,500 | 226.3 |
| 1 | 5,000 | 227.2 |
| 3 | 5,000 | 227.3 |
| 8 (comparative) | 5,000 | 221.6 |
| 10 | 5,000 | 227.5 |
| 12 | 5,000 | 228.2 |
| 14 | 5,000 | 227.6 |

Examples 17–20 demonstrate that the carbamoyl acetals have a significant nucleating effect in all of the resins tested and reduce the haze in polyolefin resin. The nucleation effect was seen at relatively low concentration, for example 500 ppm. No problem with plate out on the extrusion equipment and molds was observed, and the stability of the additive was excellent. Despite the relatively high melting temperature of most of the carbamoyl acetals, no difficulty was observed in dispersing and/or dissolving the compound in the resins tested.

The carbamoyl acetals of the present invention also find utility as gelling agents or thickening agents in unsaturated polyester resins, paints and coatings, organic solvents, such as gasoline and other petroleum products, and compositions for cosmetic and deodorant sticks.

There are, of course, many alternative embodiments and modifications of the invention which are intended to be included within the scope of the following claims.

What we claim is:

1. A compound comprising the addition product of (a) a diacetal formed by the condensation reaction of two moles of an aromatic aldehyde and a polyhydric alcohol having five or more hydroxyl groups; and (b) an isocyanate, whereby the isocyanate reacts with a free hydroxyl group of the polyhydric alcohol.

2. The compound of claim 1 wherein the polyhydric alcohol is selected from the group consisting of pentahydric and hexahydric alcohols.

3. The compound of claim 2 wherein the isocyanate is selected from the group consisting of aromatic, aliphatic and cycloaliphatic monoisocyanates.

4. The compound of claim 1 wherein the polyhydric alcohol is xylitol or D-sorbitol.

5. The compound of claim 4 wherein the isocyanate is selected from the group consisting of alkyl and cycloalkyl isocyanates.

6. The compound of claim 1 wherein the polyhydric alcohol is sorbitol and the isocyanate is selected from the group consisting of alkyl and cycloalkyl isocyanates.

7. The compound of claim 1 wherein a second mole of the isocyanate adds to a second free hydroxyl group of the polyhydric alcohol.

8. A compound having the formula:

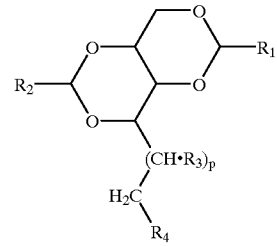

where p is 0 or 1; $R_1$ and $R_2$ are aromatic groups and may be the same or different; $R_3$ and $R_4$ are independently selected from the group consisting of —OH and —OC(O)N($R_5$)$R_6$, where $R_5$ is H, aryl, aliphatic or cycloaliphatic, and $R_6$ is H or $R_5$; and provided that at least one of $R_3$ and $R_4$ is —OC(O)N($R_5$)$R_6$.

9. The compound of claim 8 wherein $R_1$ and $R_2$ are selected from the group consisting of phenyl and phenyl substituted with from 1 to 3 $C_{1-4}$ alkyl, halo or $C_{3-5}$ alkylene forming a carbocyclic ring with adjacent carbon atoms of the phenyl ring.

10. The compound of claim 8 wherein $R_6$ is H.

11. The compound of claim 10 wherein p is 1.

12. The compound of claim 11 wherein $R_3$ and $R_4$ are —OC(O)N($R_5$)$R_6$.

13. A composition comprising a thermoplastic resin having incorporated therein from 0.005 to 3 wt. % of a compound having the formula:

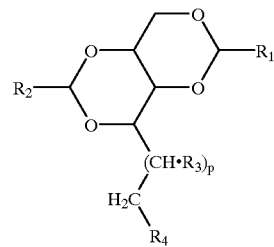

where p is 0 or 1; $R_1$ and $R_2$ are aromatic groups and may be the same or different; $R_3$ and $R_4$ are independently selected from the group consisting of —OH and —OC(O)N($R_5$)$R_6$, where $R_5$ is H, aryl, aliphatic or cycloaliphatic, and $R_6$ is H or $R_5$, and provided that at least one of $R_3$ and $R_4$ is —OC(O)N($R_5$)$R_6$.

14. The composition of claim 13 wherein the resin is selected from polyolefin, polyester, polyamide and poly(phenylene sulfide), syndiotactic polystyrene and polyketone resins.

15. The composition of claim 13 wherein p is 1 and $R_6$ is H.

16. The composition of claim 15 wherein $R_3$ and $R_4$ are selected from —OC(O)N($R_5$)$R_6$.

17. The composition of claim 16 wherein the resin is a polyolefin selected from the group consisting of polypropylene, propylene/ethylene copolymer and polyethylene.

18. The composition of claim 15 wherein the resin is a polyolefin selected from the group consisting of polypropylene, propylene/ethylene copolymer and polyethylene.

19. The composition of claim 13 wherein $R_5$ is selected from the group consisting of cyclohexyl and isopropyl, and $R_6$ is H.

20. The compound of claim 8 wherein $R_5$ is selected from the group consisting of cyclohexyl and isopropyl, and $R_6$ is H.

* * * * *